(12) United States Patent
Schmidt

(10) Patent No.: US 8,206,697 B1
(45) Date of Patent: Jun. 26, 2012

(54) DEER LURE AEROSOL DISPENSING APPARATUS

(75) Inventor: Rick Schmidt, Gambrills, MD (US)

(73) Assignee: Rick Schmidt, Gambrills, MD (US)

( * ) Notice: Subject to any disclaimer, the term of this patent is extended or adjusted under 35 U.S.C. 154(b) by 1485 days.

(21) Appl. No.: 11/466,201

(22) Filed: Aug. 22, 2006

Related U.S. Application Data

(63) Continuation-in-part of application No. 11/076,767, filed on Mar. 10, 2005, now abandoned.

(51) Int. Cl.
*A01N 25/00* (2006.01)
*A01K 97/04* (2006.01)

(52) U.S. Cl. ............... 424/84; 424/405; 426/1

(58) Field of Classification Search .................. 424/84, 424/405; 426/1
See application file for complete search history.

(56) References Cited

U.S. PATENT DOCUMENTS

| | | | |
|---|---|---|---|
| 5,083,708 A * | 1/1992 | Walters | 239/55 |
| 5,222,636 A | 6/1993 | Meuresch | |
| 5,480,095 A * | 1/1996 | Stevenson et al. | 239/104 |
| 5,555,664 A * | 9/1996 | Shockley | 43/1 |
| 5,738,851 A | 4/1998 | Colavito | |
| 6,443,434 B1 | 9/2002 | Prather | |
| 6,550,689 B1 | 4/2003 | Hoyes | |
| 6,648,239 B1 | 11/2003 | Myny | |
| 6,705,494 B2 * | 3/2004 | Thompson et al. | 222/402.15 |
| 2004/0064995 A1 | 4/2004 | Gilmore | |

FOREIGN PATENT DOCUMENTS

WO    WO 02/34636    *    5/2002

* cited by examiner

*Primary Examiner* — Benjamin Packard
*Assistant Examiner* — Adam C Milligan
(74) *Attorney, Agent, or Firm* — Ronald E. Prass, Jr.; Prass LLP

(57) ABSTRACT

A deer lure dispensing apparatus and method of use including a dispensing container containing a quantity of animal urine and a pressurized aerosol propellant. The contents are dispersed through an atomizing nozzle when a container valve is opened and locked. The lure dispensing apparatus is made to disperse its contents irrespective of its orientation. Therefore, the lure dispensing apparatus may be set to disperse, then dropped or thrown from a tree stand. It may also be inverted to spray a simulated scrape or to create a scent trail along the path a hunter walks.

6 Claims, 5 Drawing Sheets

DEER LURE AEROSOL DISPENSING APPARATUS

CROSS REFERENCE TO RELATED APPLICATIONS

This is a continuation-in-part application of U.S. Ser. No. 11/076,767, filed Mar. 10, 2005, entitled DEER LURE AEROSOL DISPENSING APPARATUS, which is incorporated by reference herein in its entirety.

BACKGROUND OF THE INVENTION

1. Field of the Invention

The present invention relates to the field of deer lure dispensing devices in general and in particular to an aerosol based deer lure dispensing apparatus with the ability to dispense the lure in any position.

2. Description of Related Art

As can be seen by reference to the following U.S. Pat. Nos. 6,443,434; 6,550,689; 6,648,239; 5,738,851, and US patent application US 2004/0064995 A1, the prior art is replete with myriad and diverse deer lure dispensing systems.

All of the aforementioned prior art constructions are more than adequate for the basic purpose and function for which they have been specifically designed. Nonetheless, they are uniformly deficient with in their failure to provide a simple, efficient, and practical method and apparatus for the molecular dispersal of a quantity of undiluted deer urine wherein air currents convey the deer lure downwind from a stand location in an effective, long distance, relatively concentrated scent cone; and in their inability to dispense the deer urine irrespective of the orientation of the dispensing container.

As most deer hunters are all too well aware, the vast majority of deer lure delivery systems fall into two broad categories which are the drag system and/or the multiple suspended wicks or ground supported wicked container system.

The major inherent problem with both these systems is the unavoidable requirement for the hunter to accompany the scent source to and along the scent dispersal trail or multiple scent stations. This restriction, even under the most rigid of scent control regimens increases the risk of human scent contamination thereby reducing the potential effectiveness of both these systems.

While the Gilmore reference, U.S. patent application number US 2004/0064995 A1, recognized the inherent deficiencies in the prior art drag and/or multiple scent wick dispersal systems, this particular arrangement also suffers from some major drawbacks of its own, particularly when employed by a bow hunter in an elevated tree stand.

The most obvious of the problems associated with the Gilmore scent dispersal system is that under most wind conditions, the scent bubbles will be carried a significant distance downwind of the hunter's stand before bursting, oftentimes not even putting down the beginning of the scent trail within a reasonable shooting distance for a bow hunter.

Furthermore, the bursting pattern of the bubbles will be random and non-uniform depending on both the wind pattern and the surrounding foliage resulting in significant breaks and different concentrations along the scent cone, which can confuse a deer attempting to follow the scent to its source.

In addition, Gilmore requires the dilution and contamination of his liquid lure base with both glycerine and water, which in the instance of tap water may have additional impurities such as fluoride or other purifying chemicals, the presence of which can be detected by a deer's olfactory receptors.

A limitation of a standard aerosol dispensing can is that the can must remain substantially upright for the contents to be dispensed properly. An apparatus for spraying pharmaceutical or cosmetic products providing for spray regardless of the orientation of the container was disclosed in U.S. Pat. No. 5,222,636. This apparatus is a pump-type spray apparatus, and would be, therefore, useless for the instant application.

As a consequence of the foregoing situation, there has existed a longstanding need among hunters in general and bow hunters in particular for a new and improved aerosol based scent dispersal apparatus that may use wind currents to put down a relatively dense and uniform molecular scent cone over a significant distance downwind from a hunter's stand location, or the lure may be applied to a surface. In these applications, the improved aerosol based scent dispersal apparatus may be oriented in any position and still accomplish the desired dispersal or application.

BRIEF SUMMARY OF THE INVENTION

Briefly stated, the deer lure aerosol dispensing apparatus that forms the basis of the present invention comprises in general a pressurized dispensing container containing an inert, odorless propellant and a quantity of pure undiluted liquid deer urine collected individually from young bucks, dominant bucks, and does both in and out of the estrous cycle.

As will be explained in greater detail further on in the specification, the dispensing container is of a type normally referred to as a fogger, capable of dispensing a pressurized aerosol mist either in short bursts or a continuous stream when the actuator lever is disposed to initiate flow and then rotated to a locked position to totally deplete the pressurized contents of the container. The container and dispensing mechanism is designed to provide dispensing in any orientation.

In the past, this type of dispensing container has been virtually exclusively employed in a closed environment wherein, the aerosol mist or fog is employed and intended to be uniformly distributed over a specific limited surface area usually for the purpose of fumigation and/or pest control.

However, the present invention has recognized that this type of aerosol dispersal system can be utilized to establish a particularly unique scent trail pattern of a significant distance wherein, the scent disposition pattern begins at the precise location of the dispensing container and continues in a virtually uninterrupted stream downwind from the location of the scent container for a distance that is primarily dependent upon the prevailing wind currents.

Additionally, the aerosol dispersal system can be used to apply the urine on a specific location. Because the aerosol container may be used in any position, it is a simple matter to aim the spray to be applied in a predetermined location.

The contents of the aerosol container may be used in a variety of ways. For instance:
1. A deer scrape may be simulated, the aerosol can inverted and sprayed over the simulated scrape to make deer believe it is a real scrape.
2. A currently existing deer scrape made by the real bucks may be enhanced by using the present invention to spray deer urine into such deer scrape.
3. A hunter may follow a path along which a deer may follow a scent trail. The aerosol can is inverted and sprayed as the hunter walks, thereby causing deer to follow the trail of deer urine once such deer have smelled it while crossing such scent trail.

4. The aerosol can may be set to dispense, and is then thrown from a tree stand thereby creating a cloud of urine scent which deer will smell and come to look for the source of the smell.

The ability to dispense the contents of the aerosol can with the can in any orientation is a key to the above uses.

As described above, it is an object of the present invention to provide an aerosol dispensing apparatus to disperse or apply an animal lure irrespective of the orientation of the aerosol dispensing apparatus.

DETAILED DESCRIPTION OF THE INVENTION

Figure 1:
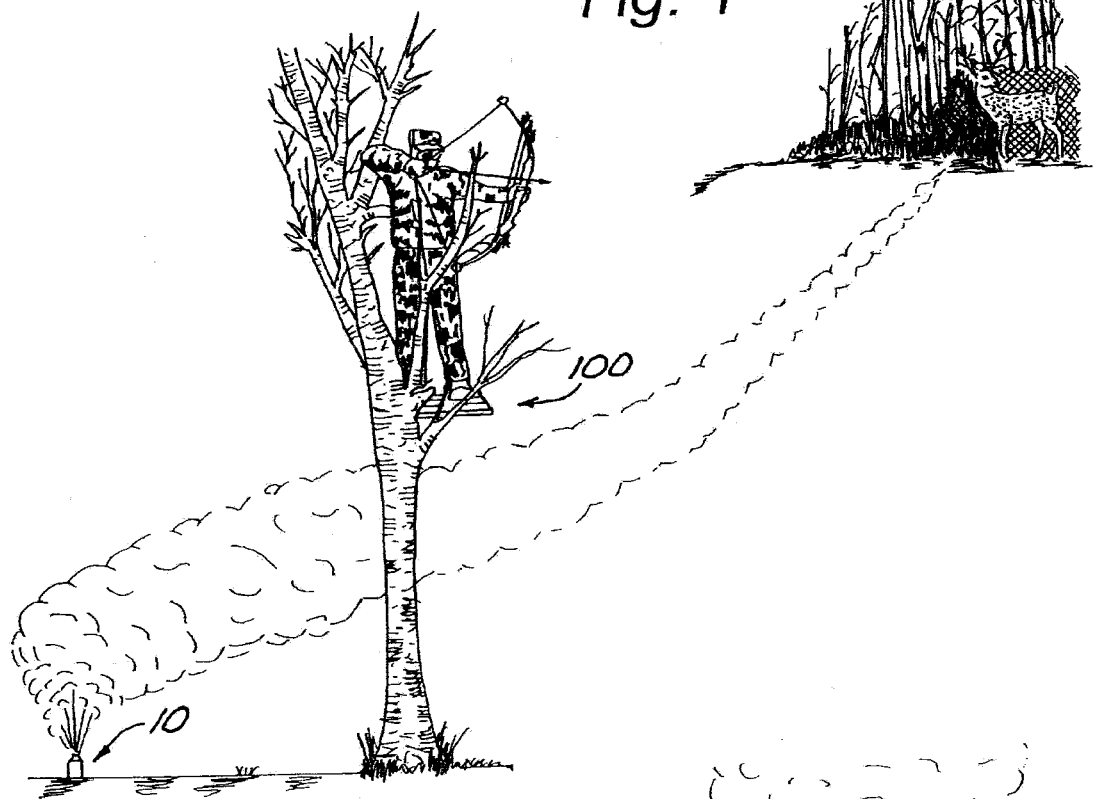
FIG. 1 is a first perspective view of the deer lure aerosol dispensing apparatus of this invention in use.
Figure 2:
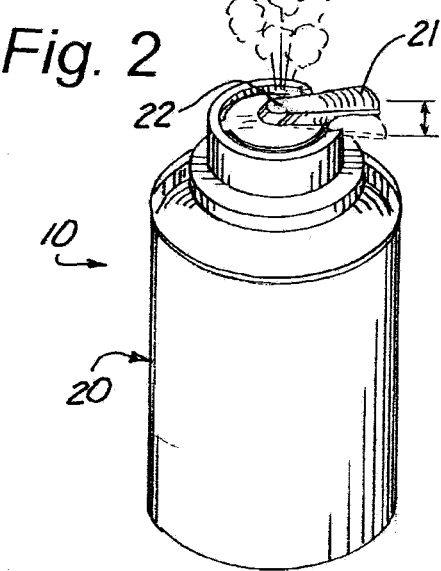
FIG. 2 is an isolated perspective view showing the apparatus in the intermittent scent dispersal mode.
Figure 3:
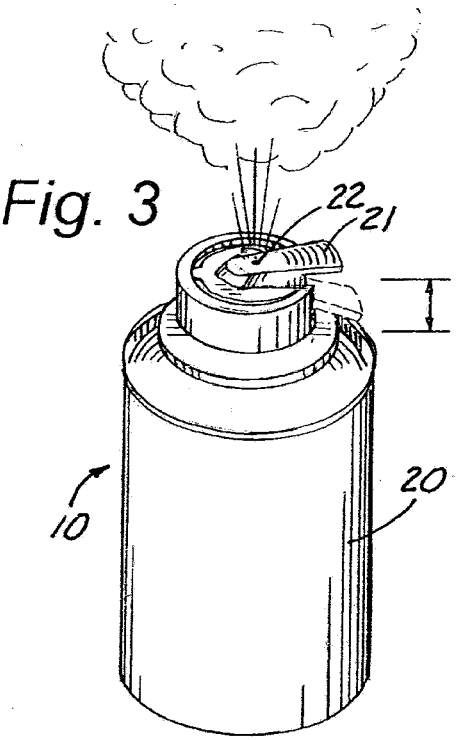
FIG. 3 is an isolated perspective view showing the apparatus in the continuous scent dispersal mode.
Figures 4, 5:
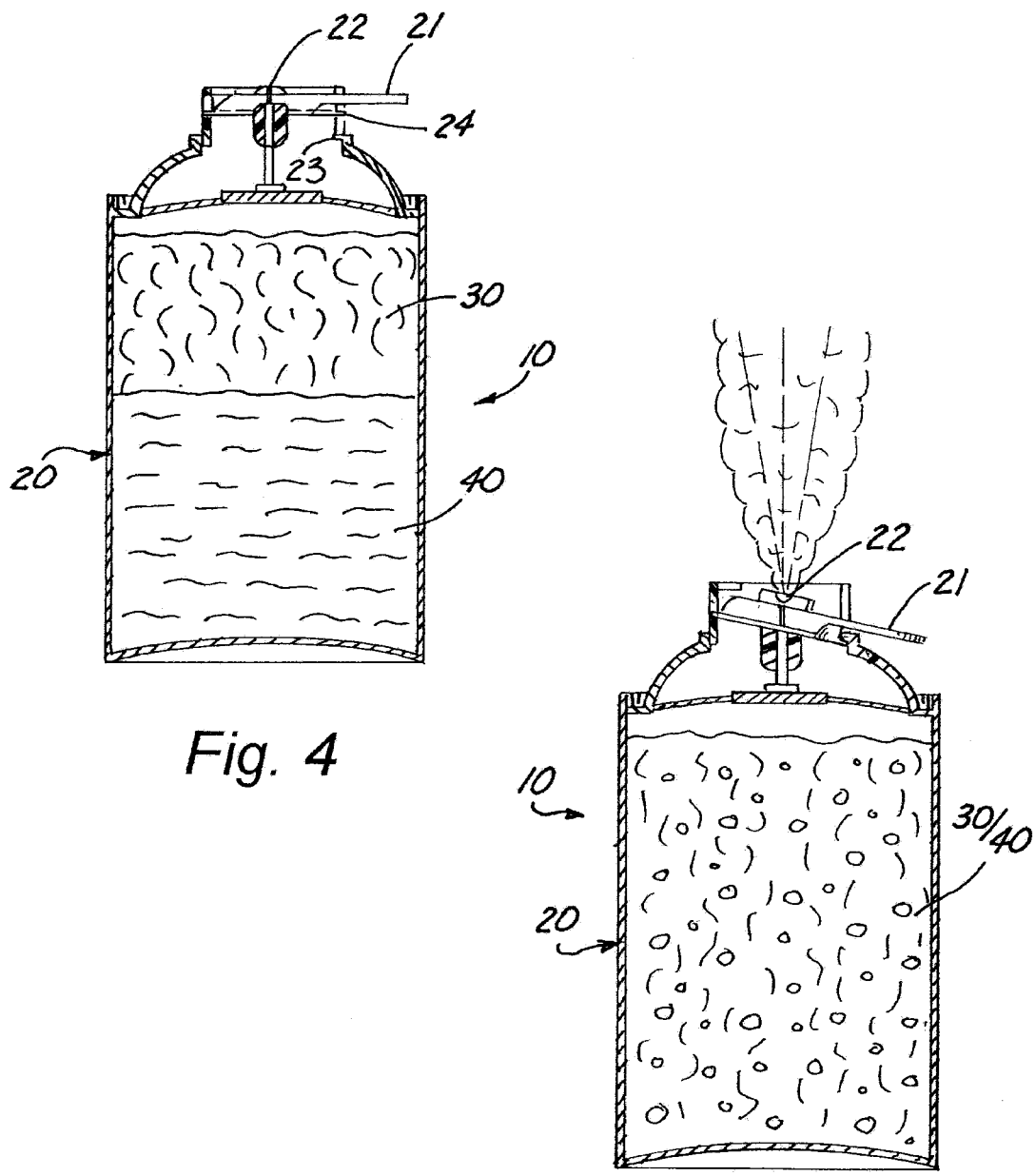
FIG. 4 is a cross-sectional view showing the contents of the dispersing container prior to shaking.
FIG. 5 is a cross-sectional view showing the mixed contents of the container during the scent dispersal phase.
Figure 6:
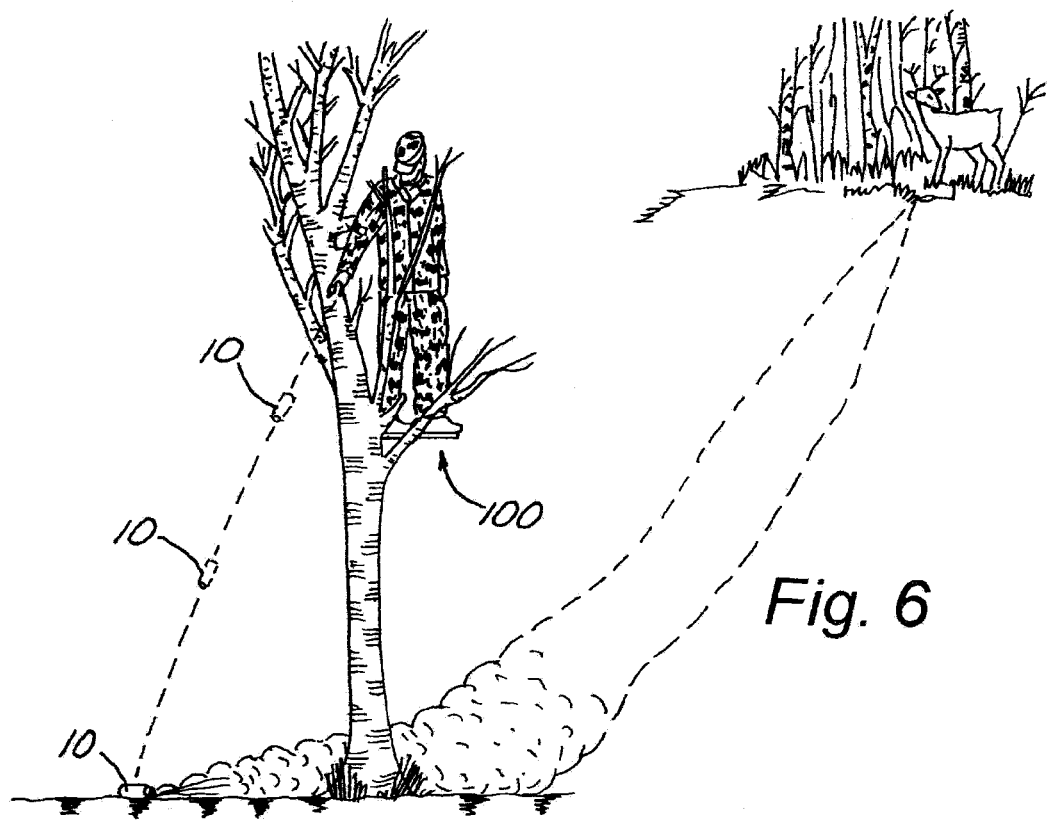
FIG. 6 is a second perspective view of the deer lure aerosol dispensing apparatus of this invention in use.

In FIG. 1, a common use for the deer lure aerosol dispersing apparatus 10 is shown. Here, a hunter is in a tree stand and the deer lure aerosol dispersing apparatus 10 is on the ground while the contents of the aerosol container 10 are dispersed. In FIG. 6, a similar setting is shown, but it is notable that the aerosol container 10, due to its ability to disperse the contents in any orientation, may be dropped or thrown from a remote location, such as the tree stand 100. This permits the hunter to remain in the tree stand 100 while the scent trail is formed.

As can be seen in FIGS. 2-5, the deer lure aerosol dispersing apparatus 10 comprises in general a dispensing container 20 containing an odorless aerosol propellant 30 and a quantity of pure, undiluted liquid animal urine 40 collected from adolescent and mature male animals, as well as female animals, both during and outside of the females' estrous cycle wherein, the liquid contents of a typical dispensing container 20 will be restricted to a specific genus of animal of a particular species and sex, and in some instances, to urine collected from a specific individual animal.

As can be seen by reference to FIGS. 2-5, the dispensing container 20 is provided with an actuator lever 21 that normally maintains an atomizing nozzle 22 in a closed position until the actuator lever 21 is depressed downwardly to release the pressurized contents of the dispensing container 20.

In addition, the actuator lever 21 is capable of being captively engaged relative to the upper portion of the dispensing container 20 which is further provided with a catch element 23, adapted to engage a tang 24 on the actuator lever 21 in its depressed position to completely deplete the pressurized contents 30, 40 of the dispensing container 20 in a continuous atomized mist.

FIG. 6 depicts a first preferred method of deployment of the lure dispensing apparatus 10 of this invention. The hunter climbs into a tree stand 100. Then the hunter vigorously shakes the contents of the dispensing container 20 to mix the ingredients 30, 40 before fully depressing and locking the actuator lever 21, thus opening the valve. After this, the hunter throws or drops the dispensing container 20 on the ground as the contents 30, 40 of the dispensing container 20 are being emptied from the container 20 and distributed into the air currents.

In addition, it would also be advisable that additional lure dispensing apparatuses 10 be carried up into the hunter's tree stand 100, either for the periodic refreshing of their initial scent trail, or to establish an entirely different new scent trail should the prevailing winds make a noticeable directional change.

Figure 7:
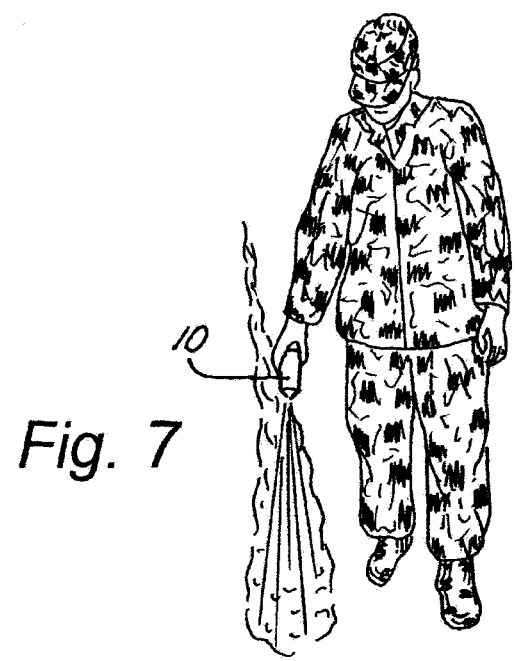
FIG. 7 is a perspective view of a hunter making a scent trail while walking.

A second preferred method of deployment of the present invention is shown in FIG. 7. The hunter follows a path on which a scent trail is desired. As the hunter walks, the lure dispensing apparatus 10 is inverted and the valve opened. The contents 30, 40 of the lure dispensing container 20 are dispersed in a scent trail along the path the hunter walks.

Figure 8:
FIG. 8 is a perspective view of a hunter providing a scent to an artificial scrape.

A third preferred method of deployment of the present invention is shown in FIG. 8. During rut, bucks will scrape the ground with their hooves and scent the area with urine. The result is called a scrape. In this third preferred method, the hunter first produces an artificial scrape 800. Then, by inverting the lure dispensing apparatus 10 and depressing and locking the actuator lever 21 to open the valve, the hunter is able to scent the artificial scrape 800 with the contents 30, 40 of the dispensing container 20.

A fourth preferred method of deployment of the present invention is also shown in FIG. 8. In this fourth preferred method, the hunter first finds a real buck scrape 800. Then, by inverting the lure dispensing apparatus 10 and depressing and locking the actuator lever 21 to open the valve, the hunter is able to scent the real scrape 800 with the contents 30, 40 of the dispensing container 20. This "freshens" the scrape so that deer are more interested in it than they would have been had this procedure not been done.

Figure 9:
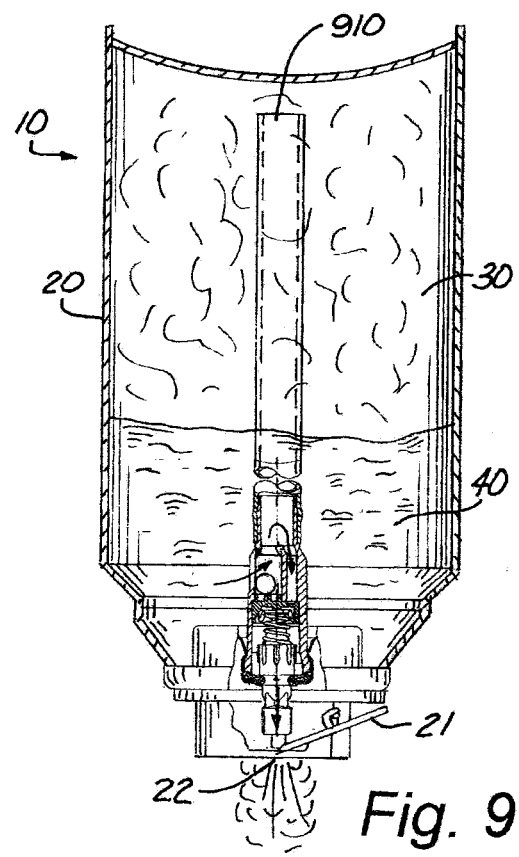
FIG. 9 is a cross-sectional view of an aerosol container dispersing its contents in an inverted position.
Figure 10:
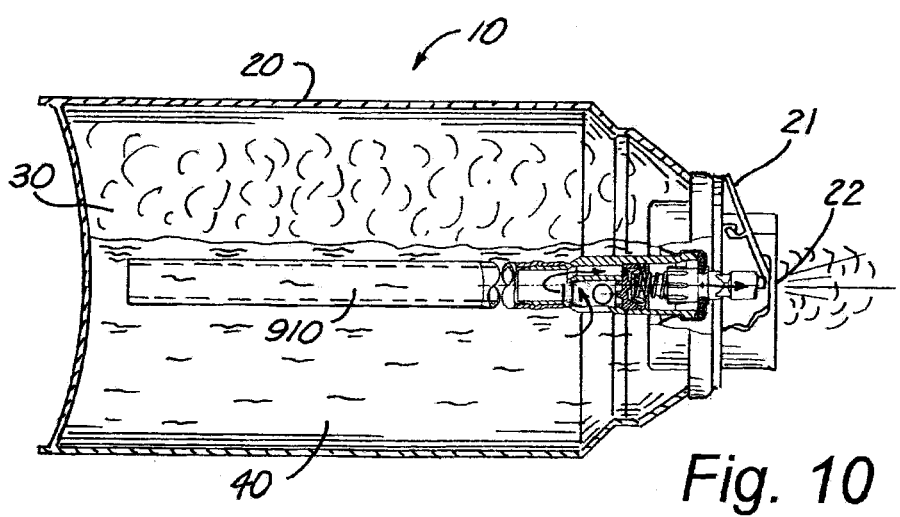
FIG. 10 is a cross-sectional view of an aerosol container dispersing its contents in a sideways position.
Figure 11:
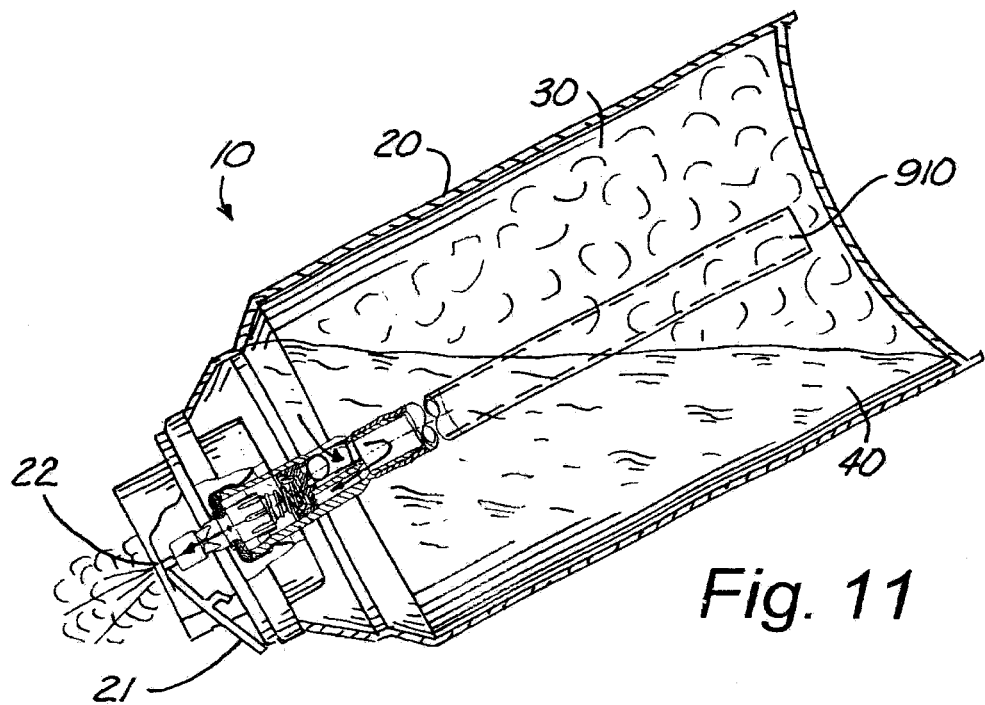
FIG. 11 is a cross-sectional view of an aerosol container dispersing its contents in a tipped position.

In FIGS. 9-11, flow paths of the contents 30, 40 of the lure dispensing container 20 are shown for various orientations of the lure dispensing apparatus 10.

Figure 12:
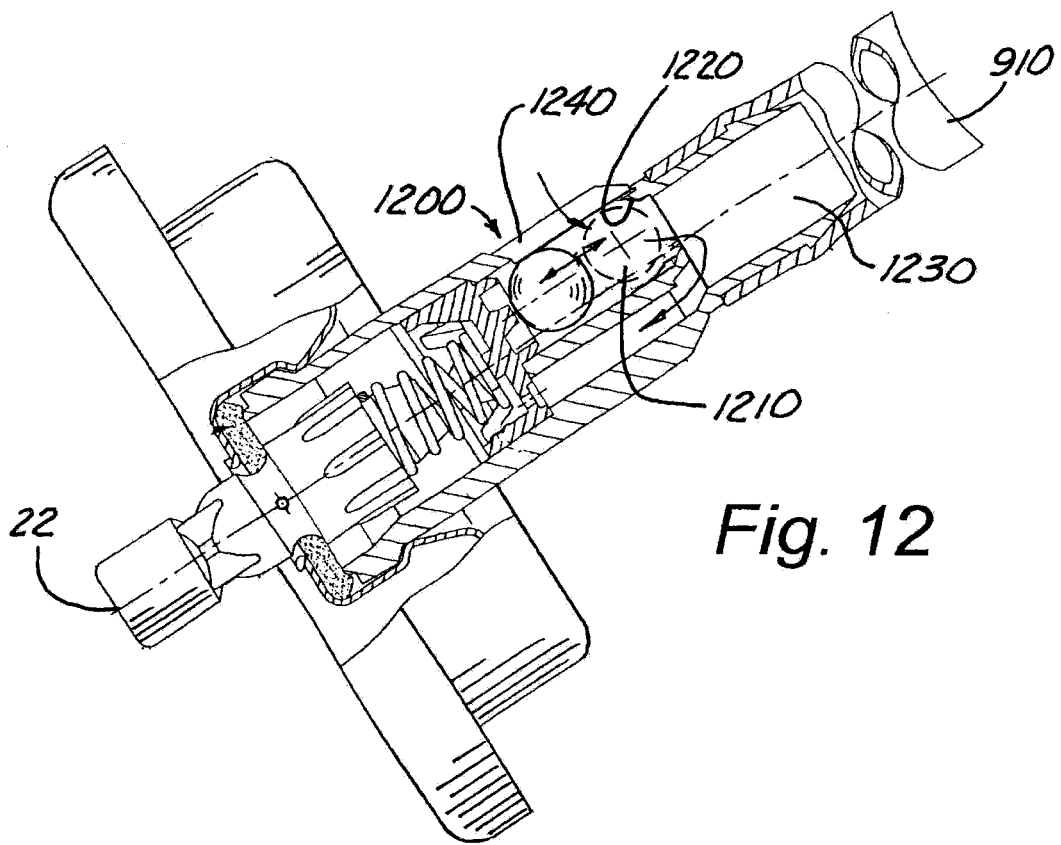
FIG. 12 is a detail of the aerosol dispenser valve.

A detail of a lure dispensing valve assembly 1200 is illustrated in FIG. 12. A selecting sphere 1210 is made to provide one of two possible flow paths, depending on the orientation of the lure dispensing apparatus 10. The selecting sphere 1210 moves toward the nozzle 22 under the force of gravity when the lure dispensing apparatus 10 is tipped or inverted. In this position, the liquid contents 40 of the lure dispensing container 20 can enter the upper entrance 1240. When the lure dispensing apparatus 10 is substantially upright, the selecting sphere 1210 moves away from the nozzle 22 under the force of gravity. In this latter position, the selecting sphere 1210 rests against a seat 1220, completely blocking the flow of the contents 30, 40 from the upper entrance 1240 and forcing the liquid portion 40 to enter the valve via the dip tube 910 and the lower entrance 1230.

Furthermore, in any of the preferred embodiments of this invention, the propellant 30 comprises dimethyl-ether pressurized to 70 psig with the atomizing nozzle 22 having a diameter of 0.016 inch and the animal urine 40 comprises between 1 and 2 fluid ounces of game animal urine.

Extensive field testing has indicated that the preferred ratio of animal urine 40 to propellant 30 should be approximately 2:1; and, in the current commercial embodiment of this invention, the interior volume of the dispensing container is 82.9 ml with the animal urine 40 accounting for 56.7 ml and the gaseous propellant 30 accounting for 26.2 ml, which generates an atomized mist issuing from the atomizing nozzle 22 at a pressure of approximately 70-75 psig.

Also this invention contemplates a pressurization range of between 65 to 85 psig and an atomizing nozzle diameter of between 0.013 to 0.030 inch.

It should also be appreciated at this juncture that in addition to the dimethly-ether, other suitable odorless propellants 40 such as carbon dioxide, butane, propane, nitrogen and tetra fluoroethane can be used.

Except for the method of scenting an artificial scrape or freshening an existing scrape, in the examples set forth supra regarding the preferred methods of using the deer lure dispensing apparatus 10 of this invention, it is presumed that ideal wind conditions such as a steady breeze of at least 5-10 miles per hour in a consistent direction exist.

When the wind conditions are less than 5 mph, it is advisable that the apparatus 10 be actuated at an elevated location closer to the height of the tree stand or hunting platform wherein the lower the wind speed, the higher the recommended height of the actuation of the apparatus 10. Suspending the lure dispensing apparatus 10 from a string, rope, twine, or wire while the lure is dispensing would accomplish this last recommendation.

This increased height under light wind conditions will ensure that there will be a sufficient downwind dispersal of the atomized contents of the dispensing container 20 to lay down an effective scent cone trail that will have the greatest chance of luring a game animal within the effective range of a hunter.

Using, as an example, a bow hunter who employs a relatively short range weapon, if the wind conditions are in excess of 10 mph, the apparatus 10 should always be actuated from ground level to ensure an effective scent trail from the point of initiation of the atomized spray. However, as previously mentioned, the lighter the wind conditions, the greater the ideal elevation for dispersal of the lure.

Essentially, the optimal height of activation of the apparatus 10 is inversely related the local wind speed.

Furthermore, while this invention has been described primarily for use with deer urine, other urine such as moose, elk, fox, coyote, and raccoon could be employed equally as well for those respective species.

Although only exemplary embodiments of the invention have been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

I claim:

1. An apparatus that attracts game animals to a particular location, comprising:
   a handheld aerosol dispensing container comprising a top and a bottom;
   animal urine contained in the handheld aerosol dispensing container; and
   an aerosol dispensing valve assembly disposed at the top of the handheld aerosol dispensing container and having an atomizing nozzle having a diameter of between 0.013 to 0.030 inch, an actuator lever, and a selecting sphere, wherein upon depression of the actuator lever, the movement of the selecting sphere enables an atomized dispensing of the animal urine from the atomizing nozzle irrespective of an orientation of the handheld aerosol dispensing container including when the bottom of the aerosol dispensing container is oriented higher than the top of the handheld aerosol dispensing container;
   a catch element that locks the actuator lever of the handheld aerosol dispensing container in an open position and permits the entire animal urine contents of the handheld aerosol dispensing container to be dispersed,
   wherein the selecting sphere provides two flow paths that depend on the orientation of the handheld aerosol dispensing container, wherein if the bottom of the handheld aerosol dispensing container is oriented higher than the top of the handheld aerosol dispensing container, the selecting sphere moves toward the atomizing nozzle under the force of gravity so that the animal urine can enter an upper entrance, and when the bottom of the handheld aerosol dispensing container is not oriented higher than the top of the handheld aerosol dispensing container, the selecting sphere moves away from the atomizing nozzle under the force of gravity so that the selecting sphere rests against a seat which completely blocks the flow of the animal urine from the upper entrance and forces the animal urine to enter the atomizing nozzle via a dip tube and a lower entrance.

2. The apparatus of claim 1, further comprising:
   a propellant contained in the handheld aerosol dispensing container, wherein the propellant comprises at least one of dimethyl-ether, carbon dioxide, butane, propane, nitrogen, and tetra fluoroethane.

3. The apparatus of claim 2, wherein a ratio of animal urine to propellant is approximately 2:1.

4. The apparatus of claim 1, wherein the animal urine in the handheld aerosol dispensing container comprises between 1 and 2 fluid ounces of game animal urine.

5. The apparatus of claim 1, wherein the optimal height of dispersion of the animal urine in the handheld aerosol dispensing container is inversely related the local wind speed.

6. The apparatus of claim 1, wherein the atomizing nozzle generates a pressurization range of between 65 to 85 psig.

* * * * *